(12) United States Patent
Aggerholm et al.

(10) Patent No.: US 10,076,398 B2
(45) Date of Patent: Sep. 18, 2018

(54) BIODEGRADABLE FILTER

(71) Applicant: Cook Medical Technologies LLC, Bloomington, IN (US)

(72) Inventors: Steen Aggerholm, St. Heddinge (DK); Kasper Klausen, Helsinge (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 125 days.

(21) Appl. No.: 13/798,938

(22) Filed: Mar. 13, 2013

(65) Prior Publication Data

US 2014/0188152 A1    Jul. 3, 2014

Related U.S. Application Data

(60) Provisional application No. 61/746,313, filed on Dec. 27, 2012.

(51) Int. Cl.
*A61F 2/01* (2006.01)

(52) U.S. Cl.
CPC ........ *A61F 2/01* (2013.01); *A61F 2210/0004* (2013.01); *A61F 2230/0069* (2013.01)

(58) Field of Classification Search
CPC ...... A61F 2/01; A61F 2/013; A61F 2002/011; A61F 2230/0067; A61F 2230/0069; A61F 2210/004; A61F 2/06; A61F 2/07; A61F 2/82; A61F 2/92; A61F 2/94; A61F 2/915; A61F 2/91; A61F 2/90; A61F 2/89; A61F 2/885; A61F 2/88; A61F 2/86; A61F 2/856; A61F 2/852; A61F 2/848; A61F 2002/061; A61F 2002/072–2002/077; A61F 2002/821–2002/828;
(Continued)

(56) References Cited

U.S. PATENT DOCUMENTS 6,267,776 B1 * 7/2001 O'Connell ............... A61F 2/01
606/158
6,517,559 B1    2/2003 O'Connell
6,582,447 B1 * 6/2003 Patel et al. .................. 606/200
(Continued)

FOREIGN PATENT DOCUMENTS

EP        2460491 A2    6/2012
WO    WO 2007/061743    5/2007
(Continued)

*Primary Examiner* — Eric Rosen
*Assistant Examiner* — Mikail Mannan
(74) *Attorney, Agent, or Firm* — Brinks Gilson & Lione (57) ABSTRACT

A filter device is provided having a biodegradable features. The filter device comprises an elongate stent portion and a conical filter portion attached thereto that is preferably balloon expandable. The conical filter portion includes a plurality of struts extending between a holding ring and the stent portion to define the conical shape of the filter portion. The struts can be biodegradable so that they degrade over time. The struts and/or holding ring can be configured so that at least one of the struts remains attached to the holding ring after a predetermined period of time. The struts are biased toward the wall of the body vessel in which the filter device is installed, so that after the predetermined period of time, the struts, and the strut attached to the holding ring, will expand toward the body vessel wall for bioabsorption.

16 Claims, 8 Drawing Sheets

(58) Field of Classification Search
CPC ............ A61F 2002/91508–2002/91591; A61F 2002/8483; A61F 2002/8486
USPC ........................................................ 606/200
See application file for complete search history.

(56) References Cited

U.S. PATENT DOCUMENTS

| | | |
|---|---|---|
| 6,972,025 B2 | 12/2005 | WasDyke |
| 8,025,675 B2 * | 9/2011 | Shirley .................... A61F 2/01 606/200 |
| 8,057,507 B2 | 11/2011 | Horan et al. |
| 8,162,970 B2 | 4/2012 | Gilson et al. |
| 8,647,360 B2 | 2/2014 | Gilson et al. |
| 8,668,713 B2 | 3/2014 | Horan et al. |
| 8,821,530 B2 | 9/2014 | Horan et al. |
| 9,017,363 B2 | 4/2015 | Binkert |
| 2008/0027481 A1 * | 1/2008 | Gilson et al. ................ 606/200 |
| 2009/0299402 A1 * | 12/2009 | Orihashi et al. ............. 606/198 |
| 2010/0016881 A1 | 1/2010 | Fleck et al. |
| 2010/0185229 A1 * | 7/2010 | Horan et al. .................. 606/200 |
| 2010/0185230 A1 * | 7/2010 | Horan ...................... A61F 2/01 606/200 |
| 2010/0228281 A1 | 9/2010 | Gilson et al. |
| 2012/0083822 A1 * | 4/2012 | Anukhin et al. ............. 606/200 |
| 2012/0143238 A1 | 6/2012 | Sogard |
| 2012/0221040 A1 | 8/2012 | Eggers |
| 2013/0226222 A1 * | 8/2013 | Eggers ......................... 606/200 |
| 2015/0150671 A1 | 6/2015 | Gilson et al. |

FOREIGN PATENT DOCUMENTS

| | | |
|---|---|---|
| WO | WO 2010/082188 A1 | 7/2010 |
| WO | WO 2010/082189 A1 | 7/2010 |

* cited by examiner

BIODEGRADABLE FILTER

CROSS-REFERENCE TO RELATED APPLICATIONS

This application claims the benefit of U.S. Provisional Application No. 61/746,313, filed on Dec. 27, 2012, entitled "BIODEGRADABLE FILTER," the entire contents of which are incorporated herein by reference.

BACKGROUND

The present invention relates to medical devices. More particularly, the invention relates to a temporary vena cava filter that can be percutaneously placed in the vena cava of a patient having biodegradable characteristics.

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

The benefits of a filtering device are known, however improvements may be made to effectively and reliably capture thrombi in a body vessel.

SUMMARY

A filter device is provided comprising: a radially expandable elongate stent portion having first and second ends; and a conical filter portion having a wide end and a narrow end, the wide end being attached to the first end of the stent portion and the narrow end being located longitudinally away from the stent portion, the filter portion being at least partially biodegradable, the filter portion comprising: a holding ring disposed at the narrow end; and a plurality of struts extending between the holding ring and the stent portion; wherein at least a portion of the plurality of struts are biodegradable and degrade after a first predetermined time to release from the holding ring; wherein at least one of the plurality of struts remains attached to the holding ring after the first predetermined period of time.

In another form, the plurality of struts are biased radially outward.

In another form, the stent portion and filter portion are balloon expandable.

In another form, the at least one of the plurality of struts that remains attached comprises a non-biodegradable rubber material.

In another form, the at least one of the plurality of struts that remains attached comprises a thick strut that is thicker than the remainder of the plurality of struts.

In another form, the at least one of the plurality of struts that remains attached comprises a tensioned strut that is tensioned relative to the remainder of the plurality of struts.

In another form, the plurality of struts are tapered, and the end of strut adjacent the stent portion is wider than the end of the strut adjacent the holding ring.

In another form, the filter device further comprises an annular support disposed at the wide end of the filter portion, the struts extend between the holding ring and the annular support, and the annular support is attached to the stent portion.

In another form, the tensioned strut is longer than the remainder of the plurality of struts.

In another form, the tensioned strut is twisted about the conical filter portion.

In another form, the at least one of the plurality of struts that remains attached is wider at its attachment to the holding ring than the remainder of the plurality of struts.

In another form, the holding ring comprises a biodegradable holding ring, and holding ring degrades at its attachment to the at least one strut that remains attached at a slower rate than at its attachment to the remainder of the plurality of struts.

In another form, the at least one of the plurality of struts that remains attached comprises a biodegradable material that degrades at a slower rate than the remainder of the plurality of struts.

In another form, the filter device further comprises a second conical filter portion attached to the second end of the stent portion.

In yet another form, a conical filter basket apparatus is provided comprising: a conical filter portion having a wide end and a narrow end, the filter portion comprising: a holding ring disposed at the narrow end; an annular support disposed at the wide end; and a plurality of struts extending between the holding ring and the annular support; wherein a portion of the holding ring is biodegradable and degrades after a first predetermined period of time to release a predetermined set of the plurality of struts attached thereto; wherein at least one of the plurality of struts remains attached to the holding ring after the first predetermined period of time.

In another form, the biodegradable portion of the holding ring comprises a plurality of holes therethrough adjacent the predetermined set of the plurality of struts.

In another form, the biodegradable portion of the holding ring comprises a biodegradable material that degrades faster than the remainder of the holding ring.

In another form, the biodegradable portion of the holding ring is thinner than the remainder of the holding ring.

In yet another form, a method for capturing thrombi in a body vessel is provided, the method comprising: compressing a filter device into a first shape, the filter device comprising: a radially expandable elongate stent portion having first and second ends; and a conical filter portion having a wide end and a narrow end, the wide end being attached to the first end of the stent portion and the narrow end being located longitudinally away from the stent portion, the filter portion being at least partially biodegradable, the filter portion comprising: a holding ring disposed at the narrow end; and a plurality of struts extending between the holding ring and the stent portion; wherein at least a predetermined set of the plurality of struts are biodegradable and degrade after a first predetermined time to release from the holding ring; wherein at least one of the plurality of struts remains attached to the holding ring after the first predetermined period of time; delivering the compressed filter device to a body vessel; expanding the stent portion into engagement with a wall of the body vessel; expanding the filter portion into its conical shape; releasing the predetermined set of the plurality of struts from the holding ring; and moving the holding ring into engagement with the wall of the body vessel after the first predetermined period of time.

In another form, the method further comprises delivering an expandable balloon disposed within the filter device to the body vessel and expanding the balloon to the expand the stent portion and the filter portion.

DETAILED DESCRIPTION

Referring now to the drawings, FIGS. 1-11B illustrate a filter device 10 for capturing thrombi in a body vessel, with the filter device 10 having a generally cylindrical stent portion 12 and a generally conical filter portion 14. As described in further detail below, the conical filter portion 14 can be made, at least partially, of a biodegradable material that will degrade over a generally predetermined time, causing the filter portion 14 to open up and become embedded in the body vessel.

The cylindrical stent portion 12 can have an elongate shape that is generally compressible and expandable in the radial direction, and can include a proximal end 12a and a distal end 12b. The stent portion 12 can be made up of a plurality of stent rings 16 that extend around the circumference of the stent portion 12 when the stent portion is in the expanded condition. The stent rings 16 can be in the form of a z-stent or other known expandable and compressible stent ring. The stent portion 12 can also include a plurality of longitudinally running support members 18 that extend along the length of the cylindrical stent portion 12. It will be appreciated that other compressible and expandable stent structures known in the art could also be used for the stent structure.

When the stent portion 12 is compressed, the stent rings 16 are compressed so that the overall diameter of the stent portion 12 is relatively small. Upon expansion, the stent rings 16 will expand, thereby increasing the overall diameter of the stent portion 12 so that the stent portion can engage the body vessel.

The stent portion 12 preferably has a substantial length, thereby providing a relative large surface area that can contact the body vessel and provide a radial force to hold the filter device 10 in place. The increased length of the stent portion 12 is preferable in this regard to shorter length devices, which included a limited contact area to provide a radial force to hold these prior devices in place.

The stent rings 16 and support members 18 defining the stent portion 12 can be made from a biodegradable or bioabsorbable metal material, such as magnesium, or from a biodegradable polymer. In one form, the stent portion 12 can be made from a composite of magnesium and polymer, having a magnesium core surrounded by a biodegradable coating or layer.

In one form, the stent portion 12 can be made from a relatively stiff polymer, while the filter portion 14 can be made from a more springy elastomeric polymer. The characteristics of the filter portion 14 will be described in further detail below.

The stent rings 16 and support members 18 are preferably sharp for promoting tissue ingrowth around the rings 16 and support members 18 when the stent has been radially expanded into engagement with the body vessel. The rings 16 and support member 18 can be laser cut to create their sharp characteristics; however, other methods of creating the sharpness can also be used.

The stent portion 12 can be either self-expandable or balloon expandable. In the case of a self-expandable structure, the stent portion 12 can be cut or cured in a manner known in the art so that its nominal shape is an expanded shape. The stent portion 12 can then be compressed within a delivery catheter for subsequent delivery, where the stent will expand back to its nominal shape upon being delivered out of the delivery device. However, compressing the stent portion 12 in this manner can lead to stress-relaxation over time, limiting the force with which it will expand when delivered. To limit the degree of stress relaxation, the stent portion 12 can be compressed and inserted into the delivery device near the time of the procedure.

Figure 1:
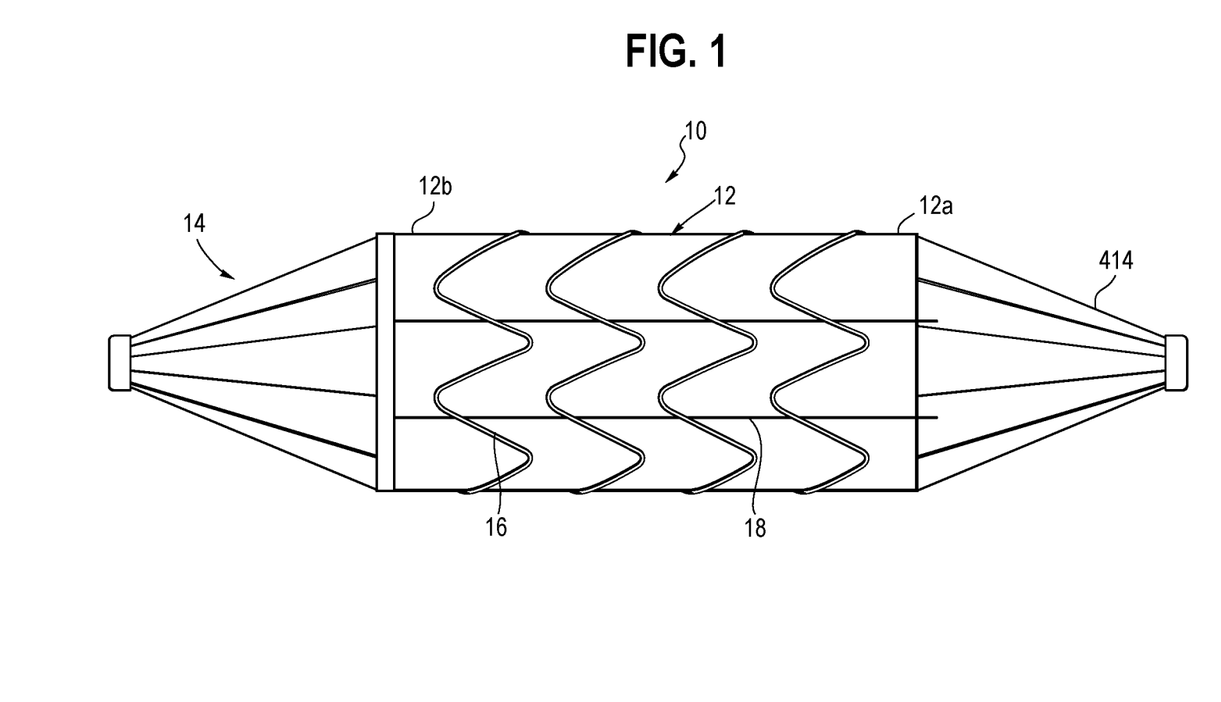
FIG. 1 is a side view of a filter device having a stent portion and a conical filter portion.
Figure 2:
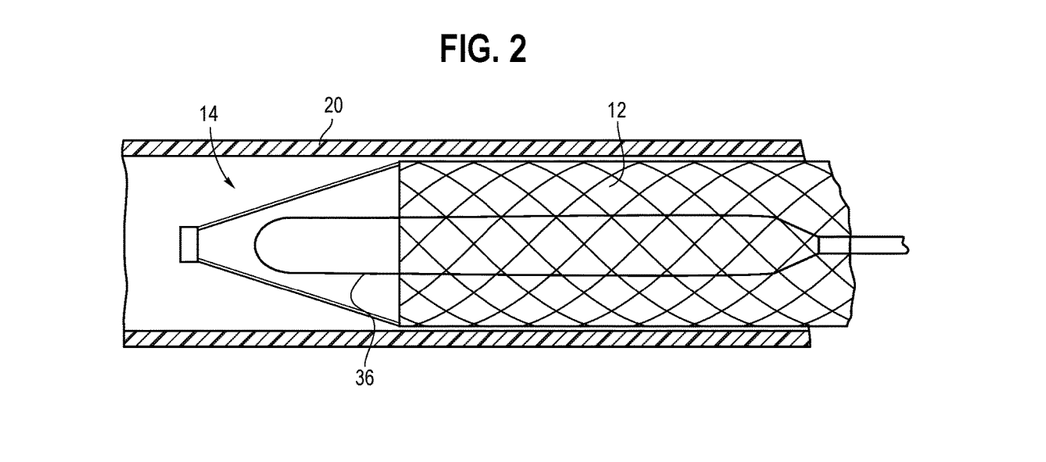
FIG. 2 is a side view of the filter device having an expandable balloon therein shown in a compressed condition within a delivery catheter.
Figure 3:
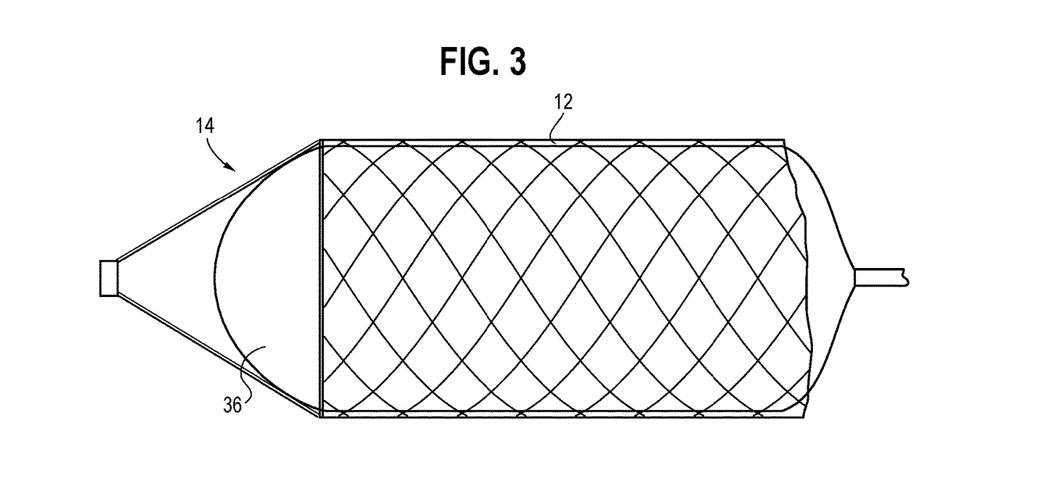
FIG. 3 is a side view of the filter device and expandable balloon shown in an expanded condition.

As shown in FIGS. 2 and 3, in a preferred form, the stent portion 12 can be balloon expandable. In this form, a balloon 36 can be inserted within the stent portion 12 with the stent portion inserted into a delivery catheter 20 in a compressed but unstressed condition (FIG. 2). When the stent portion 12 is delivered, it will not be caused to expand based on the stent portion 12 having been compressed. Rather, as shown in FIG. 3, the balloon 36, can expand in a manner known in the art (such as by filling the balloon with water or another biocompatible liquid), thereby expanding the stent portion 12 into engagement with the blood vessel, where the stent rings 16 and support members 18 can engage the wall and their sharpness will promote tissue ingrowth to keep the stent portion 12, and filter device 10, in place.

Figure 4:
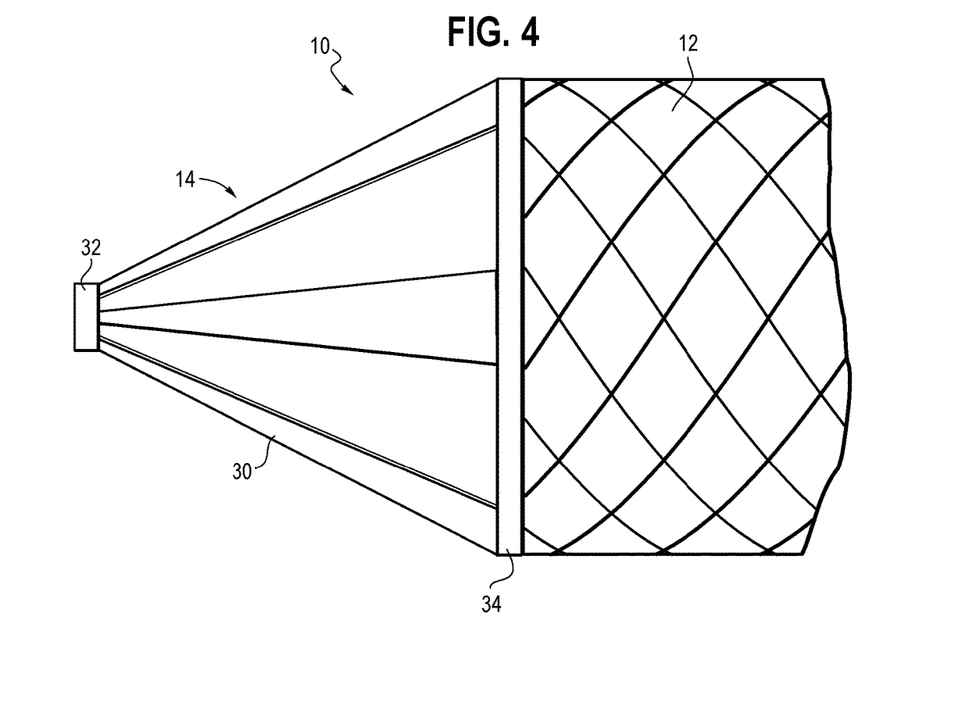
FIG. 4 is a side view of the conical filter portion having a holding ring and an annular support.

As described above, the filter device 10 includes a conical filter portion 14. The filter portion 14 includes a plurality of struts 30, where the struts 30 extend from the stent portion 12 and converge toward a holding ring 32. The holding ring 32 is a single unitary structure, as shown in FIG. 4. The struts 30 are attached to the holding ring 32, further described below, to form the conical shape of the filter portion 14. In some forms, at least some portion of the filter portion 14 is made from a biodegradable material that will degrade over a predetermined period of time, generally at a rate that ensures that the filtering needs of the patient have expired.

The struts 30 can be made from various types of material or combinations of material. The struts 30 can be made from a metallic material, such as magnesium, a biodegradable polymer material, a composite metallic and biodegradable material, or multiple types of biodegradable material having different biodegradable characteristics.

The struts 30 extend between an annular support 34 (the wide end of the conical shape) and the holding ring 32 (the narrow end of the conical shape). The struts 30 can have a generally tapered shape, having a larger width at the annular support 34 and a narrower width at their interface with the holding ring 32, as shown in FIG. 4. In the case of biodegradable struts 30, the struts 30 having a tapered shape will therefore be retained at the annular support 34 after degrading and breaking loose from the holding ring 32.

The struts 30 can be bent between the annular support and the holding ring 32 to create a stressed condition that biases the struts 30 radially away from the holding ring 32. The stressed condition can result in a buildup of potential energy within the struts 30. In the event that the struts become released from the holding ring 32 due to their biodegradable properties, the struts 30 will generally be caused to spring radially toward the blood vessel wall. However, biodegradable materials can suffer from stress relaxation over time which can affect the force with which the struts 30 expand radially outward. There are various configurations possible for counteracting the stress relaxation that can occur.

The risk of stress-relaxation can generally be a concern not because the struts 30 fail to expand fully toward the blood vessel wall, but for the holding ring 32 that holds the struts 30. Generally speaking, the struts 30 are not a concern if they do not expand fully toward the wall, because the struts are held in place at the annular support 34, and the struts 30 will continue to biodegrade. However, if the struts 30 were to each break away from the holding ring 32, the holding ring 32 would become free and travel through the blood stream. Thus, the holding ring 32 is preferably retained to at least one of the struts 30 that will expand toward the blood vessel wall, where tissue ingrowth can occur to retain the holding ring 32 along with the strut 30. The holding ring 32 can be retained in various ways, as further described below.

In each of the below described embodiments, the filter device 10, having the filter portion 14 and stent portion 12, can be expanded using balloon expansion, as described above. In addition to expanding the stent portion 12, the balloon can also extend into the filter portion 14 to expand the struts 30, as shown in FIGS. 2 and 3. The holding ring 32 will retain the struts 30 at its interface, and the expansion of the stent portion 12 will assist in expanding the struts 30 as well at the annular support 34.

Figure 5:
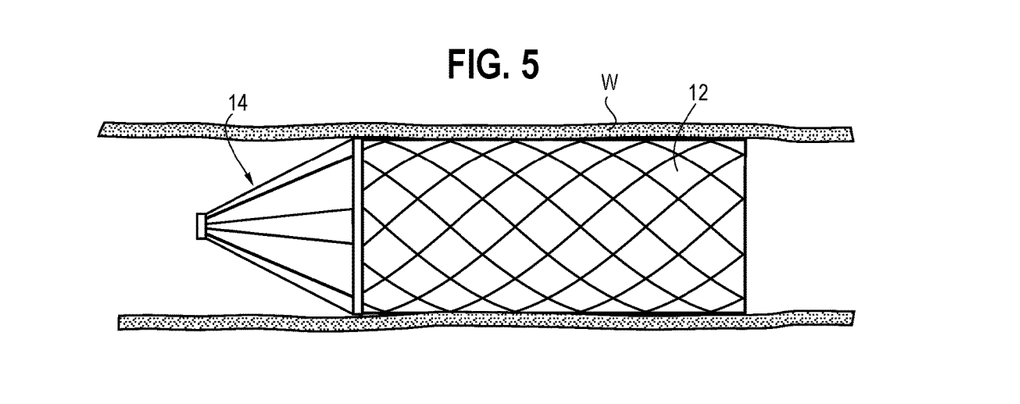
FIG. 5 is a side view of the filter device installed within a body vessel.

With reference to FIG. 5, upon expansion, the stent portion 12 will embed in blood vessel wall W where tissue ingrowth can occur. The conical filter portion 14 will operate to filter thrombi within the blood stream over an extended period of time. The extended length of the stent portion 12 will keep the filter device reliably in place. After a predetermined period of time, the struts 30 will begin to break away from the basket due to their biodegradable characteristics.

Figure 6A:
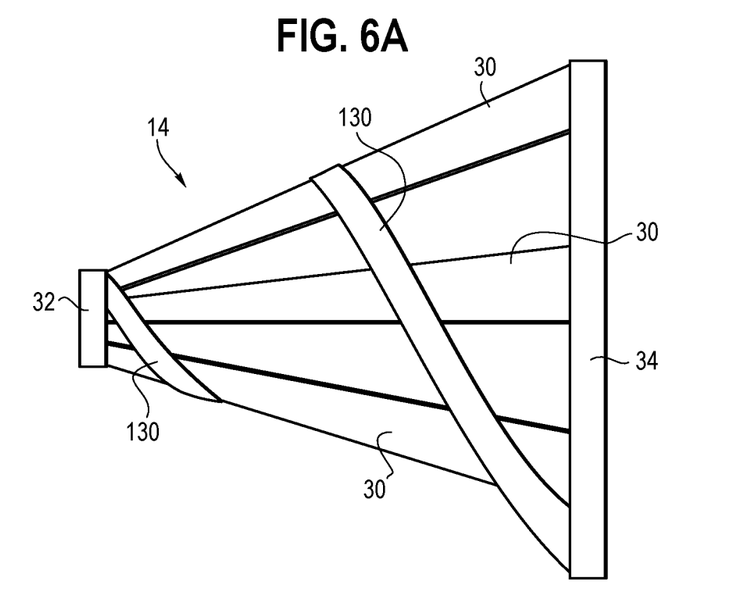
FIG. 6A is a side view of a first embodiment of the filter device.
Figure 6B:
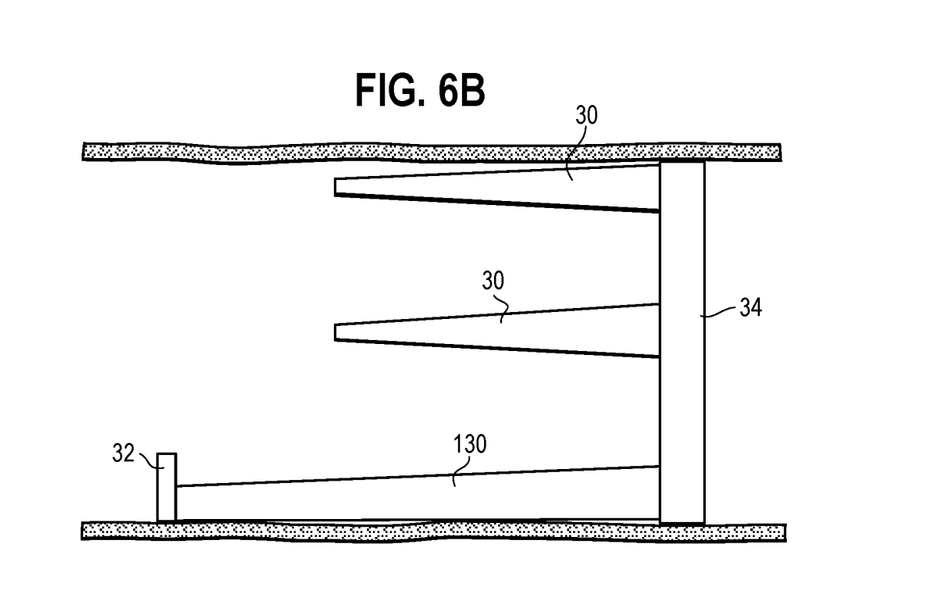
FIG. 6B is a side view of the first embodiment showing the holding ring engaged with the body vessel wall.

With reference to FIGS. 6A and 6B, in one form, the filter portion 14 includes a plurality of struts 30 as described above. The filter portion 14 also includes at least one tensioned strut 130 that is configured to degrade at a slower rate than the other struts that form the filter portion 14. The tensioned strut 130 can degrade at a slower rate by being made of the same material but thicker than the other struts 30, such that as the struts 30 and 130 degrade, the struts 30 will break away from the holding ring before the tensioned strut 130. Alternatively, the tensioned strut 130 can be made of a different material that degrades at a slower rate. It will be appreciated that other methods of altering the time at which the other struts separate from the holding ring 32 relative to the tensioned strut 130 can also be used, such as altering the tapered shape or the connection between the holding ring and the tensioned strut to increase the length of time they remain connected.

The tensioned strut 130 can be twisted or bent about the filter portion 14 so that it is held under tension. This tension will assist in retaining the springiness of the tensioned strut 130, such that when the other struts 30 break away, the tensioned strut 130 will spring toward the vessel wall, thereby retaining the holding ring 32 and moving the holding ring 32 toward and into engagement with the vessel wall, where tissue ingrowth can occur to hold the holding ring 32, as shown in FIG. 6B. While stress fatigue can still occur in the struts 30 and tensioned strut 130, the loss of tension can be mitigated or overridden by the initial tensile loading on the tensioned strut 130. Because of the twisting or bending of the tensioned strut 130 around the filter portion 14, the tensioned strut 130 can be generally longer than the other struts 30.

In addition to the above, when the struts 30 are intact with the holding ring 32, the forces on the holding ring 32 are relatively balanced and the holding ring 32 remains relatively centered. However, when the struts 30 begin breaking away, the filter portion becomes imbalanced, and the holding ring 32 will move closer to the blood vessel wall, thereby requiring less force to reach the vessel wall.

Figure 7A:
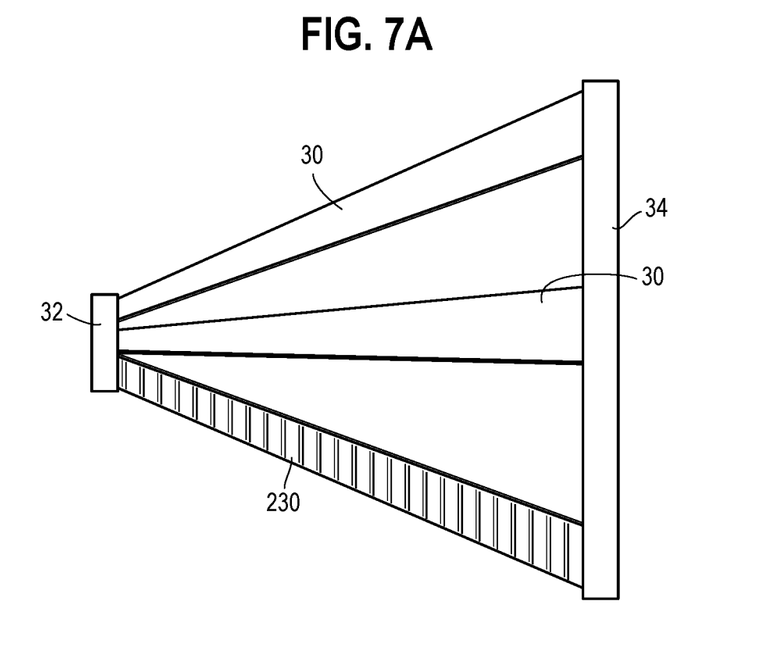
FIG. 7A is a side view of a second embodiment of the filter device.
Figure 7B:
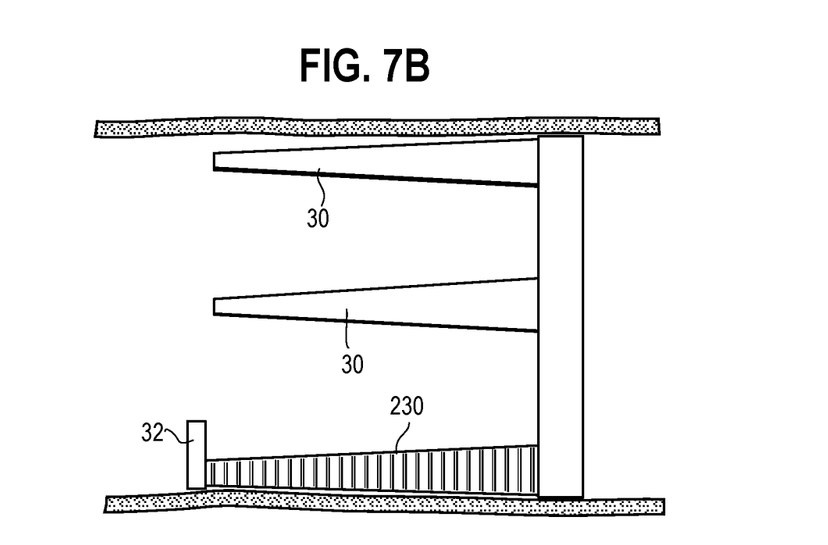
FIG. 7B is a side view of the second embodiment showing the holding ring engaged with the body vessel wall.

With reference to FIGS. 7A and 7B, in another form, the filter portion 14 can include at least one springy strut 230 made from rubber, an elastomeric material, or a rubber-like material that is generally not biodegradable, but is preferably biocompatible such that it can become implanted in the blood vessel wall. While it is not required that the springy strut 230 be made from a bioabsorbable/biodegradable material, it could be so long that it has increased springiness relative to the other struts 30. While the remaining struts 30 will still degrade over time, the rubber strut 230 will not. Thus, the rubber strut 230 could be used in the same manner as the tensioned strut 130, described above, because the rubber strut 230 will remain attached to the holding rind 32 after the other struts 30 have degraded. However, the characteristics of the rubber strut 230 can allow it to be used without twisting or bending the rubber strut 230. The properties of the rubber strut 230 will allow it to retain its springiness relative to biodegradable struts 30 that suffer more from stress fatigue.

As shown in FIG. 7B, as the struts 30 break away from the holding ring 32, the springy strut 230 will remain attached to the ring 32. The springy strut 230 will thus spring toward the blood vessel wall with the holding ring 32 retained, where the holding ring 32 can embed into the wall and tissue ingrowth can occur.

Figure 8A:
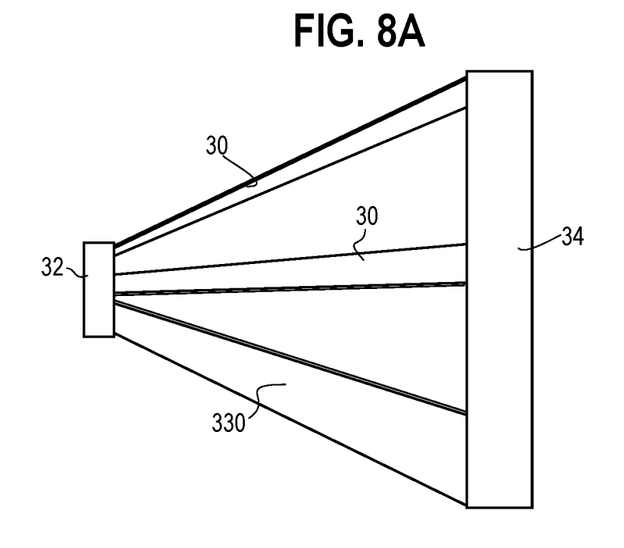
FIG. 8A is a side view of a third embodiment of the filter device.
Figure 8B:
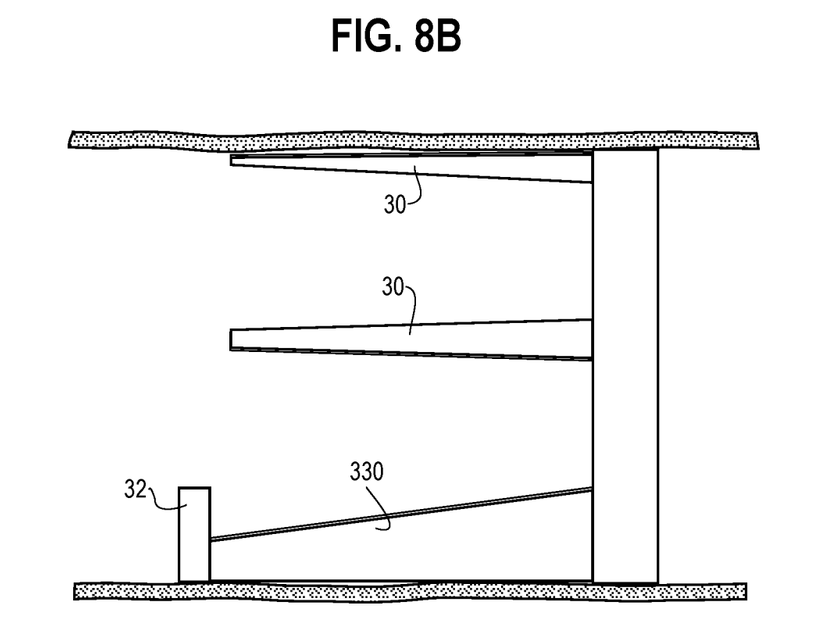
FIG. 8B is a side view of the third embodiment showing the holding ring engaged with the body vessel wall.

With reference to FIGS. 8A and 8B, in another form, a thick strut 330 can be used in addition to the struts 30 previously described above. The thick strut 330 can be generally made from the same material as the struts 30 so they degrade at the same rate, but the thicker strut 330 will remain intact with the holding ring 32 longer because of its added thickness. As the other struts 30 break away from the holding ring 32, they will tend to spring away toward the blood vessel wall. Additionally, the filter portion 14 will become imbalanced and the holding ring 32 will shift toward the vessel wall. The thick strut 330 will remain attached to the holding ring 32, so that when the thick strut 330 outlasts the other struts 30, it will move toward the vessel wall, where tissue ingrowth can occur.

Figure 8C:
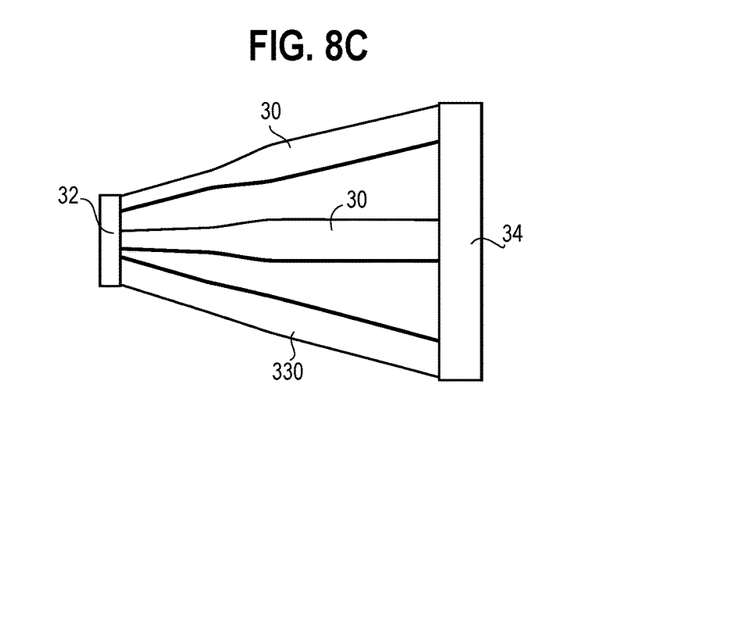
FIG. 8C is a side view of a fourth embodiment of the filter device.

Alternatively, as shown in FIG. 8C, the thick strut 330 could include a smaller amount of tapering, where the thickness at the annular support 34 was the same as the struts 30, but thicker at the attachment to the holding ring 32.

Figure 9A:
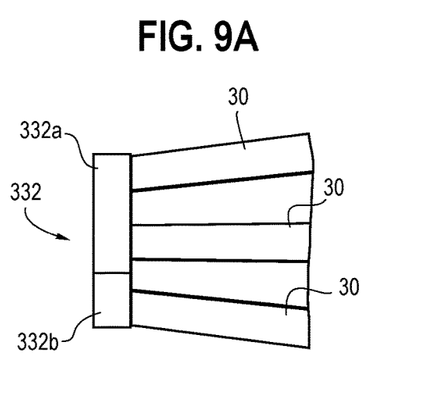
FIG. 9A is a side view of another embodiment of the holding ring.
Figure 9B:
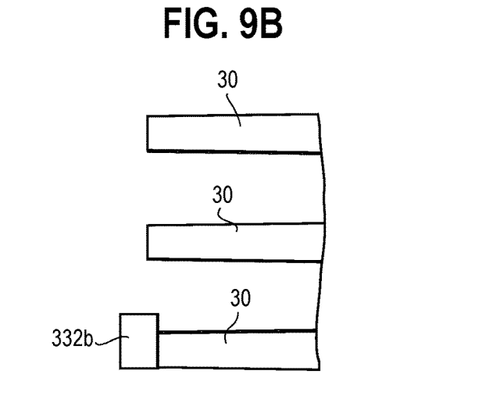
FIG. 9B is a side view of the holding ring of FIG. 9A showing the holding ring attached to one of the struts after the other struts are detached.

With reference to FIGS. 9A and 9B, in another form, a holding ring 332 could be used in addition to or in lieu of different strut structures. The holding ring 332 is a single unitary structure and the entire ring 332 is biodegradable. The holding ring 332 can be formed to break away from similarly configured struts 30 at different rates. In one form, the holding ring 332 can be formed of different biodegradable material along a first portion 332a of the ring 332 compared to a second portion 332b. The first portion 330a can be attached to all but one of the struts 30, with the second portion being attached to the remaining strut 30, as shown in FIG. 9A. The first portion 330 can degrade first, causing the struts 30 attached thereto to separate first, leaving the second portion 330b still attached to the remaining strut 30, as shown in FIG. 9B. The holding ring 332 will then shift toward the vessel wall along with the strut 30 that remains attached thereto.

Figure 10A:
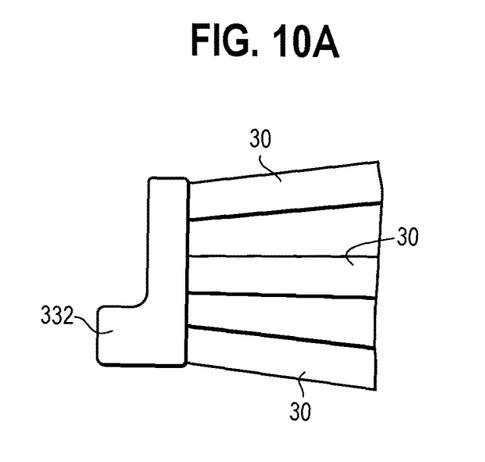
FIG. 10A is a side view of yet another embodiment of the holding ring.
Figure 10B:
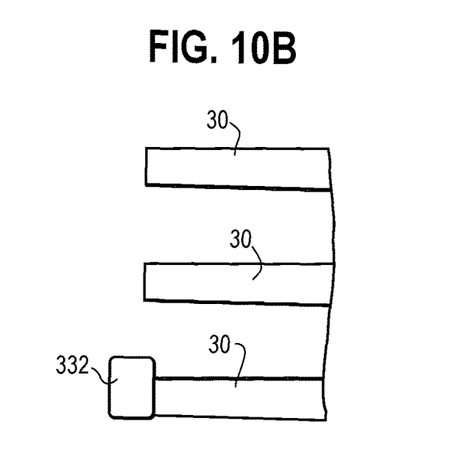
FIG. 10B is a side view of the holding ring of FIG. 10A showing the holding ring attached to one of the struts after the other struts are detached.

With reference to FIGS. 10A and 10B, in another form, the holding ring 332 can be made thinner at the first portion 330a relative to the second portion 330b. Similarly to the above, the holding portion 330 will remain attached to the strut 30 that is attached to the second portion 330b, and the holding ring will shift toward the wall due to the strut 30 that remains attached.

Figure 11A:
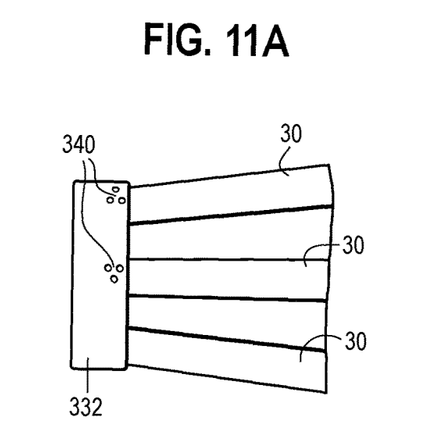
FIG. 11A is a side view of yet another embodiment of the holding ring.
Figure 11B:
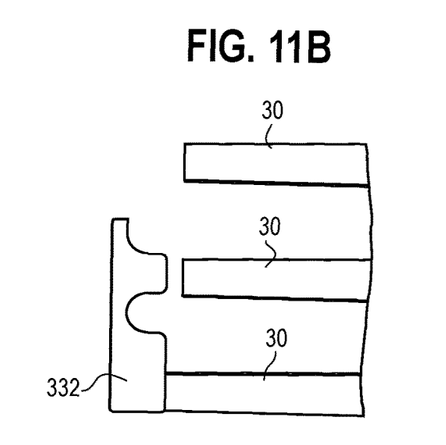
FIG. 11B is a side view of the holding ring of FIG. 11A showing the holding ring attached to one of the struts after the other struts are detached.

With reference to FIGS. 11A and 11B, in another form, the holding ring 332 can include a plurality of holes 340 disposed therethrough and located adjacent to the struts 30 that are attached. The plurality of holes 340 will cause the holding ring 332 to degrade at a faster rate at that area, thereby causing the struts 30 to become detached relative to struts 30 that are attached to the holding ring 332 free from adjacent holes 340. Thus, the holding ring 332 can remain attached to one of the struts 30 after the others have become detached, and the attached strut 30 will shift the holding ring 332 toward the blood vessel wall, where tissue ingrowth can occur.

With reference again to FIG. 1, each of the above concepts can include a second filter 414 disposed at the opposite end of the stent portion 12.

It will be appreciated by a person skilled in the art that numerous combinations and permutations of the above concepts are possible, leading to myriad possibilities for controlling the degradation of the filter device 10 and the conical filter portion 14.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A filter device comprising:
   a radially expandable elongate stent portion having first and second ends; and
   a conical filter portion having a wide end and a narrow end, the wide end being attached to the first end of the stent portion and the narrow end being located longitudinally away from the stent portion, the filter portion being at least partially biodegradable, the filter portion comprising:
   a holding ring disposed at the narrow end; and
   a plurality of struts extending between the holding ring and the stent portion;
   wherein at least a portion of the plurality of struts are biodegradable and degrade before a first predetermined time to release from the holding ring;
   wherein at least one of the plurality of struts remains attached to the holding ring after the first predetermined period of time.

2. The filter device of claim 1, wherein the plurality of struts are biased radially outward.

3. The filter device of claim 1, wherein the stent portion and filter portion are balloon expandable.

4. The filter device of claim 1, wherein the at least one of the plurality of struts that remains attached comprises a non-biodegradable rubber material.

5. The filter device of claim 1, wherein the at least one of the plurality of struts that remains attached comprises a thick strut that is thicker than the remainder of the plurality of struts.

6. The filter device of claim 1, wherein the at least one of the plurality of struts that remains attached comprises a tensioned strut that is tensioned relative to the remainder of the plurality of struts.

7. The filter device of claim 6, wherein the tensioned strut is longer than the remainder of the plurality of struts.

8. The filter device of claim 7, wherein the tensioned strut is twisted about the conical filter portion.

9. The filter device of claim 1, wherein the plurality of struts are tapered, and the ends of the plurality of struts adjacent the stent portion are wider than the ends of the plurality of struts adjacent the holding ring.

10. The filter device of claim 1 further comprising an annular support disposed at the wide end of the filter portion, the struts extend between the holding ring and the annular support, and the annular support is attached to the stent portion.

11. The filter device of claim 1, wherein the at least one of the plurality of struts that remains attached is wider at its attachment to the holding ring than the remainder of the plurality of struts.

12. The filter device of claim 1, wherein the holding ring comprises a biodegradable holding ring, and the biodegradable holding ring degrades at its attachment to the at least one strut that remains attached at a slower rate than at its attachment to the remainder of the plurality of struts.

13. The filter device of claim 1, wherein the at least one of the plurality of struts that remains attached comprises a biodegradable material that degrades at a slower rate than the remainder of the plurality of struts.

14. The filter device of claim 1 further comprising a second conical filter portion attached to the second end of the stent portion, wherein the second conical filter portion includes a second plurality of struts, and the first plurality of struts extends longitudinally away from the stent portion and the second plurality of struts extends longitudinally away from the stent portion and in an opposite longitudinal direction than the extension of the first plurality of struts.

15. A method for capturing thrombi in a body vessel, the method comprising:
   compressing a filter device into a first shape, the filter device comprising:
   a radially expandable elongate stent portion having first and second ends; and
   a conical filter portion having a wide end and a narrow end, the wide end being attached to the first end of the stent portion and the narrow end being located longitudinally away from the stent portion, the filter portion being at least partially biodegradable, the filter portion comprising:
   a holding ring disposed at the narrow end; and
a plurality of struts extending between the holding ring and the stent portion;
   wherein at least a predetermined set of the plurality of struts are biodegradable and degrade before a first predetermined time to release from the holding ring;
   wherein at least one of the plurality of struts remains attached to the holding ring after the first predetermined period of time;
   delivering the compressed filter device to a body vessel;
   expanding the stent portion into engagement with a wall of the body vessel;
   expanding the filter portion into its conical shape;
   releasing the predetermined set of the plurality of struts from the holding ring; and
   moving the holding ring into engagement with the wall of the body vessel after the first predetermined period of time.

16. The method of claim 15 further comprising delivering an expandable balloon disposed within the filter device to the body vessel and expanding the balloon to expand the stent portion and the filter portion.

* * * * *